United States Patent
Sato et al.

[11] Patent Number: 5,743,258
[45] Date of Patent: Apr. 28, 1998

[54] PHARYNGEAL AIRWAY

[75] Inventors: Toru Sato, Yonago; Minoru Shibata; Shiro Agehama, both of Akita, all of Japan

[73] Assignee: Mallinckrodt Medical, Inc., St. Louis, Mo.

[21] Appl. No.: 586,912
[22] PCT Filed: May 30, 1995
[86] PCT No.: PCT/JP95/01043
§ 371 Date: Jan. 26, 1996
§ 102(e) Date: Jan. 26, 1996
[87] PCT Pub. No.: WO95/32754
PCT Pub. Date: Dec. 7, 1995

[30] Foreign Application Priority Data

May 31, 1994 [JP] Japan .................................. 6-118169

[51] Int. Cl.⁶ .................................................. A61M 16/04
[52] U.S. Cl. ........................... 128/207.15; 128/207.14; 128/200.26; 128/911; 128/912; 128/DIG. 26
[58] Field of Search ........................ 128/200.26, 207.15, 128/207.14, 911, 912, DIG. 26

[56] References Cited

U.S. PATENT DOCUMENTS

| | | | |
|---|---|---|---|
| 4,449,523 | 5/1984 | Szachowicz et al. | 128/200.26 |
| 4,739,756 | 4/1988 | Horn | 128/207.15 |
| 5,146,916 | 9/1992 | Catalani | 128/207.15 |
| 5,287,848 | 2/1994 | Chubb et al. | 128/200.26 |
| 5,372,131 | 12/1994 | Heinen | 128/207.15 |
| 5,443,063 | 8/1995 | Greenberg | 128/207.15 |
| 5,499,625 | 3/1996 | Frass et al. | 128/207.15 |

*Primary Examiner*—Vincent Millin
*Assistant Examiner*—William J. Deane, Jr.
*Attorney, Agent, or Firm*—Rothwell, Figg, Ernst & Kurz, P.C.

[57] ABSTRACT

A pharyngeal airway tube, without inserting any foreign matters in the trachea (T), can be easily inserted through the oral cavity (O) in the lower pharynx (P), and is capable of hermetically sealing a transitional region from the lower pharynx to the esophagus (E) and the periphery of the laryngeal opening (AL) to secure an airway for positive pressure artificial ventilation. The pharyngeal airway comprises an airway tube (1) having a closed, round distal end and provided in its side wall with ventilating holes (2), and a balloon (3) attached to the edge of the ventilating part and around the ventilating part of the airway tube and capable of being inflated so as to surround a part of the airway tube near the distal end of the same. A small bore gas passage (4) is formed in the wall of the airway tube so as to open into the balloon, and a small bore tube (5) fitted with a connector (7) is connected to the proximal end of the gas passage.

18 Claims, 5 Drawing Sheets

PHARYNGEAL AIRWAY

TECHNICAL FIELD

The present invention relates to an airway device for securing a respiratory air-route necessary for the respiration of an unconscious patient. More specifically, the present invention relates to a medical airway implement for securing the respiratory route for a patient, that is for securing an adequate airway from the mouth through the pharynx to enable the unconsious patient to inspire or expire air, or oxygen and anesthetic gases easily so that the patient can be ventilated from the pharynx to the trachea and then finally to the lungs, and especially for facilitating intermittent positive pressure artificial ventilation as needed, without using any tracheal tube during general anesthesia or while the patient is in a comatose condition.

BACKGROUND ART

Currently available medical implements to secure an airway for anesthesia, emergency resuscitation or the management of seriously ill patients include tracheal tubes, oropharyngeal airways, nasopharyngeal airways, esophageal obstructor airways (EOAs), laryngeal masks (LMs) and the like.

Tracheal tubes have been most prevalently used because tracheal tubes surely secure a respiratory route, facilitate the evacuation of endotracheal secretion, isolate the airway from gastric contents regurgitated through the esophagus and enables positive pressure artificial ventilation without any troubles as needed when tracheal tubes are inserted orally or nasally in patients' tracheae and connected to anesthetic machines, lung ventilators or resuscitators etc.

When surely inserting a tracheal tube in the patient's trachea for emergency resuscitation, the intubation of the tracheal tube in a routine manner requiring direct vision of the larynx with a laryngoscope is liable to entail serious adverse effects due to neural reflex actions, such as arrhythmia and the regurgitation of gastric contents. Thus, the intubation of the tracheal tube is a highly risky, invasive medical practice which can be safely performed only by a physician skilled in the endotracheal intubation procedures.

Furthermore, stimulation of the very sensitive pharynx and oppression of the delicate ciliary epithelium in the trachea with the tracheal tube and its inflated cuff cause foreign sensation in the throat, hoarse voice and difficulty in expectoration and, in the worst case, entails serious complications, such as glottic edema and/or tracheitis. Accordingly, it is a recent medical trend to avoid, if possible, inserting any foreign matters in the larynx and the trachea for the purpose of securing adequate airway. Oropharyngeal and nasopharyngeal airways have been prevalently used for many years.

However, such an airway is not satisfactorily effective because such a short airway device is inserted simply in the throat to hold the root of the tongue mechanically with its tip so as to prevent airway obstruction by depression. Since the airway is unable to fully support the total structure of the tongue root, the use of the airway, in most cases, is not satisfactorily effective.

Furthermore, the airway cannot prevent regurgitation from the esophagus into the trachea and also requires hermetically holding a face mask and the patient's jaw by hands during artificial respiration.

Therefore, the airway can be applied effectively to limited cases and can be safely used only for a limited time. However, it is a significant advantage of the airway that the airway, unlike the tracheal tube, can be used by nurses and ambulance paramedics as well as physicians skilled in airway manipulation.

Esophageal obstructor airways (EOAs) have been manufactured in U.S. and have been prevalently used worldwide by ambulance personnel. An EOA, unlike tracheal tubes, does not require direct laryngoscopy. When using the EOA, the tube of the EOA is inserted blindly and quickly in the esophagus, a balloon attached to a part of the tube near the distal end of the same is inflated in the lower esophagus so that the balloon comes into close contact with the esophageal wall, thus the lower part of the esophagus is obstructed with the blind distal end of the tube and the inflated balloon to prevent the regurgitation of gastric contents and to secure a hermetic condition, and then air is introduced through the side holes of the tube into the esophagus to force air into the larynx and the trachea for artificial respiration.

When using an EOA provided with a face mask, the face mask must be held in close contact with the patient's face in a hermetic state by both hands, otherwise, the face mask cannot be held in a hermetic state on the patient's face. Therefore, it is difficult to perform positive pressure artificial respiration satisfactorily in a travelling ambulance. Furthermore, since the EOA must be used in combination with a face mask, the EOA is unsuitable for use in many surgical operations, anesthesia and intensive care, and is used mainly by ambulance personnel for the short-period emergency resuscitation of moribund patients.

The laryngeal mask (LM) invented by Archibald I. J. Brain, a medical doctor of London, U.K. (UK Patent No. 2,111,394) has been introduced into U.S. and Japan, and has been used in anesthesia and emergency resuscitation. The LM is formed by attaching a rubber mask to the open end of a thick, arched tube. When using the LM, the laryngeal opening (aditus laryngis) is covered with the inflated silicone rubber mask. The LM has been gradually diffused in the clinical field since the LM was introduced and its clinical applications have been published by Brain in a paper on "The Laryngeal Mask" in Br. J. Aneasth, 1983 by Amaha, et al. "MASUI (Jap. J. of Anesthesia)" and so on in many medical journals. An improved LM invented by incorporating a moderate bore tube for removing the liquid collected in the mask region by suction or siphonage is disclosed in Japanese Patent Laid-open No. 2-283378 (Nov. 20, 1990), which, however, has not yet been commercialized.

The LM has attracted worldwide attention in the clinical field because the LM does not need the insertion of any foreign matters in the trachea, can be conveniently used in general anesthesia under spontaneous respiration only if the LM is set correctly except when the patient is in a prone position in which the management of respiration is difficult, and the LM is safe to use and does not entail postoperative complications. However, it is not necessarily easy to set the LM at a correct working position in the absence of spontaneous respiration, and also it is difficult to perform effective positive pressure artificial ventilation because of gas leakage through the periphery of the rubber mask when airway pressure exceeds a certain level (about 30 cmH$_2$O) during intermittent positive pressure artificial ventilation because the rubber mask cannot be pressed against the laryngeal opening in the pharyngeal cavity by a pressure high enough to withstand such a high airway peak pressure, and the regurgitation of the gastric contents and the flow of the gastric contents into the trachea (aspiration) cannot be perfectly avoided. Although nurses and first-aid paramedics, as well as medical doctors, are licensed or allowed to use the LM in Japan, a sufficient pressure for intermittent positive pressure artificial ventilation for emergency resuscitation can be hardly applied to the patient when the LM is used and it is difficult to determine a correct depth of the insertion and thus a correct application position for the LM.

The present invention has been made in view of the foregoing circumstances and it is therefore an object of the present invention to provide a pharyngeal airway, without inserting any foreign matters in the trachea, which can be easily inserted through the mouth to the lower pharynx to obstruct a transitory part between the lower pharynx and the esophagus, and it is capable of hermetically sealing the laryngeal opening to secure an airway for positive pressure intermittent artificial ventilation.

DISCLOSURE OF THE INVENTION

A pharyngeal airway in accordance with the present invention comprises: an arched airway tube having a bevelled opening formed by diagonally cutting the distal end thereof; and a balloon formed of a soft, elastic thin film, connected to the circumference of the open end and a portion near the distal end of the airway tube and capable of being inflated so as to surround a portion of the airway tube near the distal end, or in the shape of a double-wall balloon formed of an inner balloon within the balloon, or two balloons, i.e., a first balloon capable of being inflated in a ring shape so as to surround a portion near the distal end of the airway tube and a second balloon capable of being inflated in a hemispherical shape around a portion of the distal end of the airway tube defining the bevelled opening. Each of these balloons is formed so as to maintain a naturally bulged shape of a size greater than that of the laryngeal opening when the atmospheric pressure prevails therein. When inserting the airway tube in the mouth, the balloon is inserted through the lower pharynx toward the esophagus after shrinking the balloon by evacuating the same with negative pressure. When the interior of the balloon is opened to the atmosphere after setting the balloon almost in place, the distal portion of the balloon inflates naturally. The balloon is fully inflated in the hemispherical shape after the balloon has been set in contact with the upper esophageal sphincter to prevent the regurgitation of gastric contents through the esophagus, so as to be in close contact with the periphery of the laryngeal opening and with the pharyngeal mucosa in an airtight state with the bevelled opening of the airway tube held toward the laryngeal opening.

When the airway tube of the pharyngeal airway of the present invention is inserted through the mouth into the lower pharynx, the arched distal end of the tube is made straight and the round distal end in an anteriorly bevelled shape extends along the backside of pharynx so as not to enter the laryngeal opening located in front of the distal end or not to catch uneven portions at the periphery thereof and thereby being inserted into the esophagus securely. Then a naturally inflated balloon disposed near the rounded distal end of the airway tube can be hardly passed through the upper esophageal sphincter so as to limit the further insertion of the airway tube and a ventilating part formed in a concave or anterior surface near the distal end of the airway tube easily coincide with the laryngeal opening. In this state, air is supplied through a gas supply passage formed in the airway tube to the balloon connected to a portion of the airway tube around the bevelled opening and around the edge of the opening to inflate the balloon so that a transitional region from the lower pharynx to the esophagus and a region around the laryngeal opening are sealed. Thus, the pharyngeal airway of the present invention is safe, reliable and easy to use, and can be effectively used as an implement for emergency artificial ventilation.

Since the balloon of the pharyngeal airway of the present invention has a distal part capable of maintaining a naturally bulged shape on the distal side of the ventilating part, and a proximal part capable of maintaining a naturally shrunk shape on the proximal side of the ventilating part, the airway tube can be easily inserted in the pharyngeal cavity in co-operation with the shape of the distal end and can be surely positioned at a correct position since the distal end of the slightly bulged balloon with the atmospheric pressure catches the sphincter of the upper esophagus.

Since the airway tube of the pharyngeal airway of the present invention is provided with a plurality of elongate ventilating holes formed and arranged in an even array so that the ventilating holes may not reduce much the anti-bending strength of the airway tube, the airway tube can be smoothly inserted in the lower pharynx and has a sufficient anti-bending strength.

When the airway tube of the pharyngeal airway of the present invention is internally provided along its longitudinal axis with a suction tube having a distal end opening in the distal end of the airway tube and a proximal end connected to a suction connector, gases and gastric juices regurgitated through the esophagus can be removed by suction, or drainage whereby the flow of the regurgitated matters into the respiratory tract can be surely avoided.

BEST MODE FOR CARRYING OUT THE INVENTION

The present invention will be described in detail hereinafter with reference to the accompanying drawings.

Figure 1:
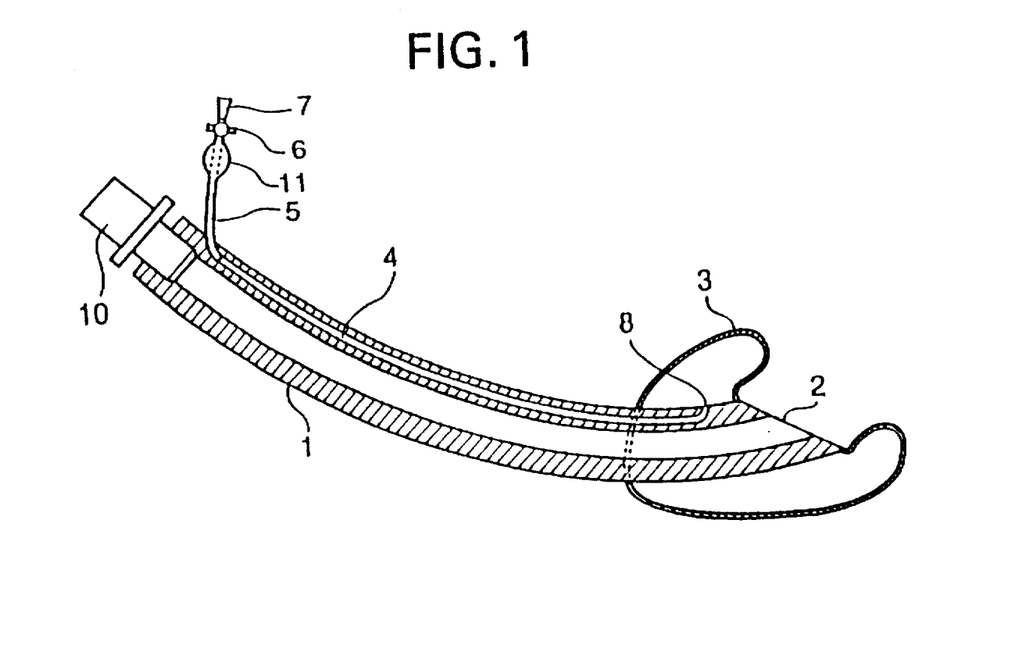
FIG. 1 is a longitudinal sectional view of a pharyngeal airway in a first embodiment according to the present invention.
Figure 2:
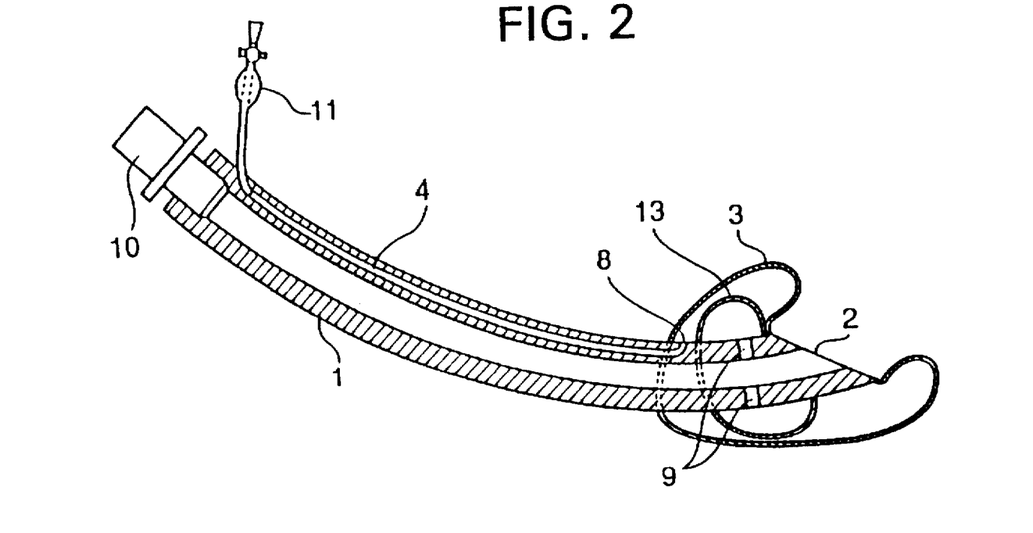
FIG. 2 is a longitudinal sectional view of a pharyngeal airway in a second embodiment according to the present invention.
Figure 3:
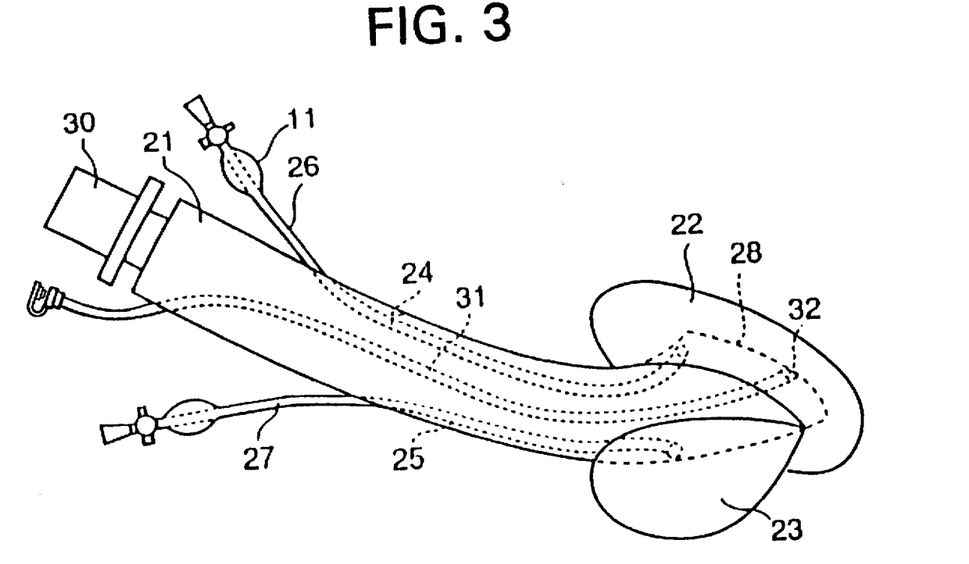
FIG. 3 is a longitudinal sectional view of a pharyngeal airway in a third embodiment according to the present invention.
Figure 4:
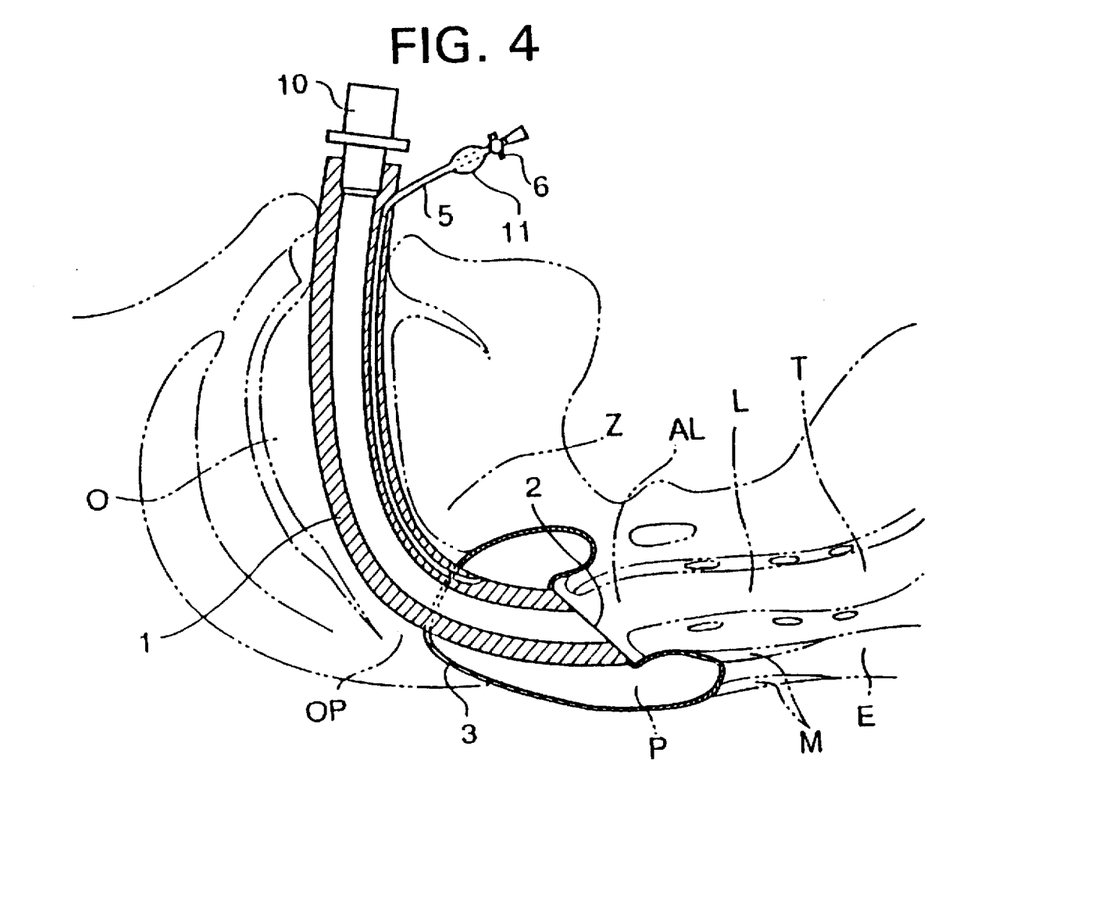
FIG. 4 is a longitudinal sectional view of assistance in explaining a mode of using a pharyngeal airway according to a first embodiment of the present invention.

FIGS. 1 to 3 show pharyngeal airways in a first, second and third embodiments, respectively, according to the present invention, and FIG. 4 shows one of the pharyngeal airways shown in FIGS. 1 to 3 in use of the first embodiment.

Referring to FIG. 1 showing the pharyngeal airway in the first embodiment in a longitudinal sectional view, a wide bore airway tube 1 has a distal end diagonally cut to form a bevelled opening 2, and a proximal end fitted with a connector 10 communicating with the interior of the airway tube 1. The connector 10 is connected to a resuscitator or the like. A balloon 3 is capable of being inflated in a substantially hemispherical shape so as to surround a distal part of the airway tube 1 and to extend behind the distal end of the airway tube 1, being connected to the edge of the opening 2 and the outer surface of the airway tube 1.

A longitudinal small bore gas passage 4 for passing a gas to inflate or shrink the balloon 3 is formed in the wall of the airway tube 1 so as to open in a pore 8 within the balloon 3. A tube 5 of a small diameter is connected to the proximal end of the gas passage 4, and a cock 6 provided with an adaptor 7 and a pilot balloon is fitted in the free end of the tube 5.

Referring to FIG. 4, when inserting the airway tube 1 of the pharyngeal airway through the oral cavity O into the lower pharynx P, the balloon 3 attached to the distal end of the airway tube 1 is flattened by evacuation and is coated with a lubricant to facilitate the passage of the airway tube 1 through the oropharyngeal cavity OP because the oropharyngeal cavity OP is curved approximately at a right angle, and is pressed and narrowed by the root Z of the tongue.

After the distal end of the airway tube 1 has reached the lower pharynx P, the cock 6 fitted in the tube 5 is opened. Consequently, the atmospheric pressure prevails in the balloon 3 and the balloon 3 is allowed to inflate naturally, so that a part of the balloon 3 around the opening 2 of the airway tube 1 bulges slightly. Therefore, the airway tube 1 can be easily and surely advanced through the lower pharynx P behind the laryngeal opening AL (Aditus laryngis) as far as the distal end of the airway tube 1 comes into contact with esophageal sphincter M in the upper part of the esophagus E. Then, a gas is supplied through the tube 5 and the gas passage 4 into the balloon 3 to inflate the balloon 3 at a moderate pressure so that a region from the esophagus E to the lower pharynx P is sealed by the balloon 3. Since the balloon 3 is flexible and is capable of inflating in all directions, i.e., longitudinally, transversely and backwardly, without covering the opening 2 of the airway tube 1, the entire surface of the lower pharynx P through the oropharyngeal cavity OP is sealed gently, and the wide opening 2 is pressed against the laryngeal opening AL to secure an airway from the oral cavity O through the lower pharynx P to the larynx L.

When the connector 10 meeting the international standards for connecting to positive pressure artificial respiration devices is connected to a resuscitator, and a gas, i.e., air or oxygen, is forced intermittently into the airway tube 1, the gas flows through the airway tube 1 and is forced to flow through the bevelled opening 2 and the larynx L into the trachea T for inspiration. When the pressure is removed, a gas flows in the reverse direction for expiration into the atmosphere.

Figure 5:
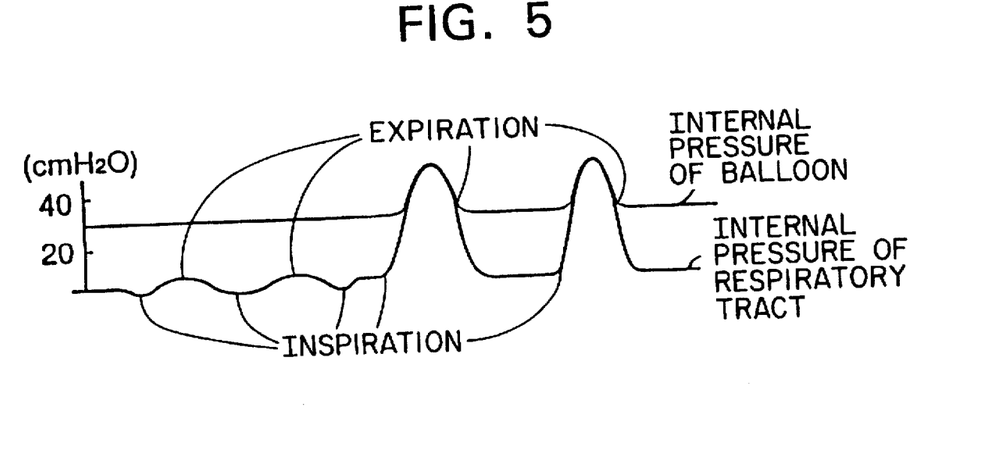
FIG. 5 is a diagram showing the relation between the internal pressure of the respiratory tract and the internal pressure of the balloon during intermittent positive pressure ventilation by using a pharyngeal airway in accordance with the present invention.

The balloon 3 is formed of a soft, stretchable thin film so that the balloon 3 conforms closely to the undulated mucosa forming the surface of the lower pharynx for airtight sealing under the atmospheric pressure when the pressure of the gas in the balloon 3 is about 30 cm $H_2O$ or below and is capable of achieving perfect sealing without injuring the mucosa in contact therewith. When conducting intermittent positive pressure artificial ventilation by intermittently applying a gas pressure above that pressure through the airway tube 1, the gas pressure, i.e., a positive pressure in the respiratory tract, acts through the opening 2 of the airway tube in contact with the periphery of the laryngeal opening AL on the outer surface of the balloon 3, so that the flexible balloon 3 is locally deformed and compressed and the internal pressure of the balloon 3 is raised intermittently to a pressure equal to the pressure prevailing in the respiratory route as shown in FIG. 5, whereby the airtightness can be naturally secured.

FIG. 2 shows a pharyngeal airway in a second embodiment according to the present invention intended to change the internal pressure of a balloon 3 intermittently by changing the internal pressure of the balloon 13. The pharyngeal airway shown in FIG. 2 is basically the same in construction as the pharyngeal airway shown in FIG. 1, except that the former is provided within the balloon 3 with an inner balloon 13 formed of a stretchable thin film, and one or a plurality of side holes 9 formed in a portion of an airway tube 1 enclosed in the inner balloon 13 to interconnect the interior of the inner balloon 13 and that of the airway tube 1.

When a connector 10 attached to the proximal end of the airway tube 1 is connected to a resuscitator and a gas, i.e., air or oxygen, is supplied intermittently into the airway tube 1 for positive pressure artificial ventilation, the gas flows through the holes 9 into the inner balloon 13, and the pressure of the gas acts directly on the inner surface of the inner balloon 13 to inflate the inner balloon 13.

Consequently, the internal pressure of the balloon 3 increases accordingly and the balloon 3 expands uniformly in all directions without being locally deformed. Therefore, the balloon 3 does not move relative to the mucosa in contact with the balloon 3 and injures the mucosa scarcely, whereby the pharyngeal airway can be securely held in the lower pharynx.

Referring to FIG. 3 showing a pharyngeal airway in a third embodiment according to the present invention, a wide bore, arched airway tube 21 has, similarly to the airway tube 1 shown in FIG. 1, a bevelled distal end diagonally cut to form a bevelled opening 28, and a proximal end fitted with a connector 30 communicating with the interior of the airway tube 1. The connector 30 is connected to a resuscitator or the like. A first balloon 22 capable of being inflated in a ring shape so as to surround the bevelled opening 28 and a part of the airway tube 21 extending behind the bevelled opening 28 is connected to the distal end of the airway tube 21, and a second balloon 23 capable of being inflated in a hemispherical shape is attached to the surface of the airway tube 21 opposite the bevelled opening 28.

Small bore longitudinal gas passages 24 and 25 for passing a gas to inflate or shrink the balloons 22 and 23 are formed in the wall of the airway tube 21 so as to open into the balloons 22 and 23, respectively. Tubes 26 and 27 of a small diameter are connected to the proximal ends of the gas passages 24 and 25, respectively, and cocks each provided with an adaptor and a pilot balloon are fitted in the free end of the tubes 26 and 27, respectively. As shown in FIG. 3, a suction passage 31 for sucking out gastric and esophageal discharges may be formed from position near the proximal end of the airway tube 21 fitted with the connector 30 through the wall of the airway tube 21 so as to open in a suction opening 32 at the distal end of the airway tube 21. Preferably, the suction passage 31 has a diameter in the range of about 3 to about 5 mm and a circular or an elliptic cross section.

The pharyngeal airway shown in FIG. 3 is provided with two balloons 22 and 23 capable of being individually inflated and shrunk, instead of the single balloon 3 of the pharyngeal airway shown in FIG. 1. Referring to FIG. 4, when the airway tube 21 is inserted through the oral cavity O in the lower pharynx P, the first balloon 22 is capable of being inflated in a ring shape so as to surround the laryngeal opening AL hermetically, and the second balloon 23 is capable of being inflated in a hemispherical shape at a position on the airway tube 21 opposite the bevelled opening 28 toward the rear side of the lower pharynx P. When using the pharyngeal airway, the airway tube 21 is inserted in the pharynx with both the balloons 22 and 23 evacuated to shrink the balloons 22 and 23 to the least possible size, the insertion of the airway tube 21 is stopped when the distal end of the airway tube 21 reaches the lower pharynx P and the naturally inflated balloons 22 and 23 come into light contact with the esophageal sphincter M in the upper part of the esophagus E narrowing from the lower portion of the larynx. After confirming that air is flowing through the respiratory tract, the first balloon 22 is inflated and positive pressure artificial respiration is started. If the gas leaks at a high rate, then a gas is supplied to the second balloon 23 to press the first balloon 22 against laryngeal opening AL at the proximal level of the esophagus to enhance the airtightness between the laryngeal opening AL and the first balloon 22 so that the sealing effort of the first balloon 22 is able to withstand the maximum inspiratory pressure for pressure respiration.

Even if the gas staying in the stomach and the gastric juice regurgitate, the leakage of the gas and the gastric juice into the respiratory tract can be prevented. The gas and the gastric juice can automatically escape to the atomospher or be positively removed by suction through the suction passage 31.

There is no particular restriction on the materials forming the airway tubes and the balloons of the pharyngeal airways in accordance with the present invention, and the airway tubes and the balloons may be formed of any suitable materials generally used for manufacturing medical implements, provided that those materials are highly safe, soft and flexible; soft vinyl resins and silicon rubbers are suitable materials. The balloon 3 of the first embodiment shown in FIG. 1 having a part naturally maintaining a bulged shape and other part maintaining shrunk shape under the atmospheric pressure, and the balloons 22 and 23 of the third embodiment shown in FIG. 3 naturally maintaining bulged shapes or shrunk shapes, respectively, can be easily formed by selectively determining the thickness and the hardness of the material forming the balloons 3, 22 and 23.

Figure 6:
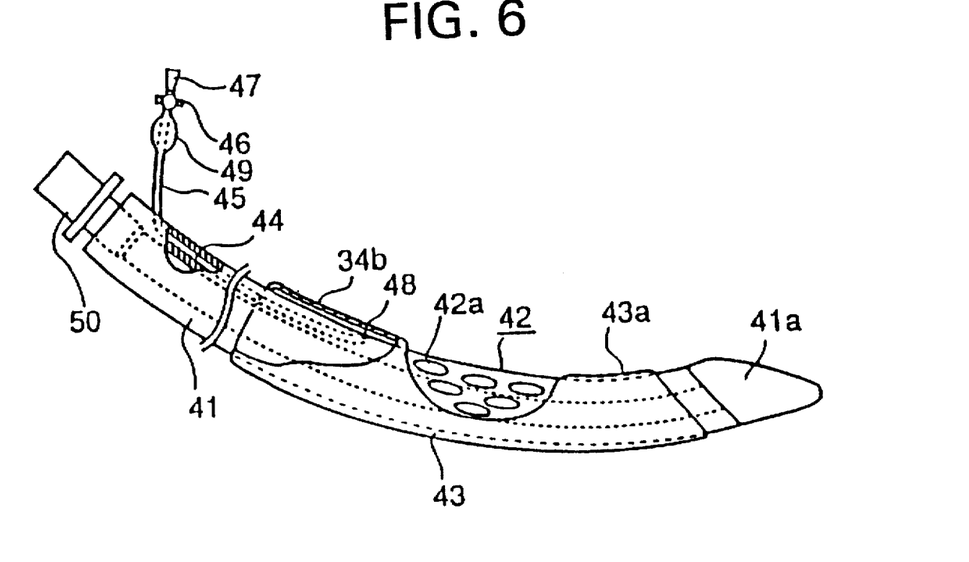
FIG. 6 is a lateral view of a pharyngeal airway in a fourth embodiment according to the present invention.
Figure 7:
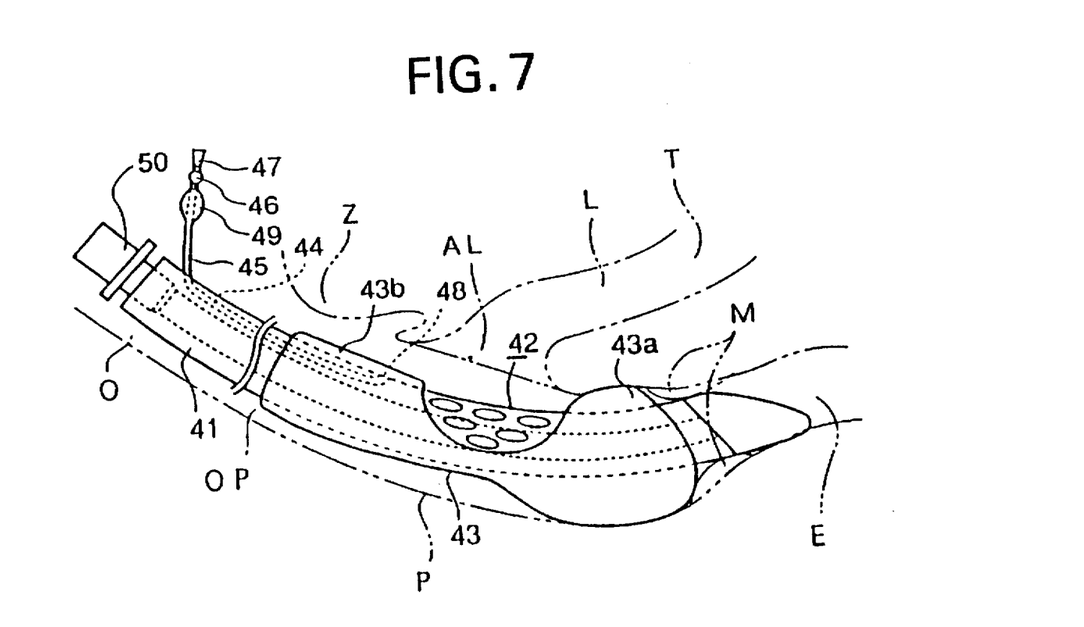
FIG. 7 is a lateral view of the pharyngeal airway of FIG. 6 in a state where the balloon is being slightly inflated.
Figure 8:
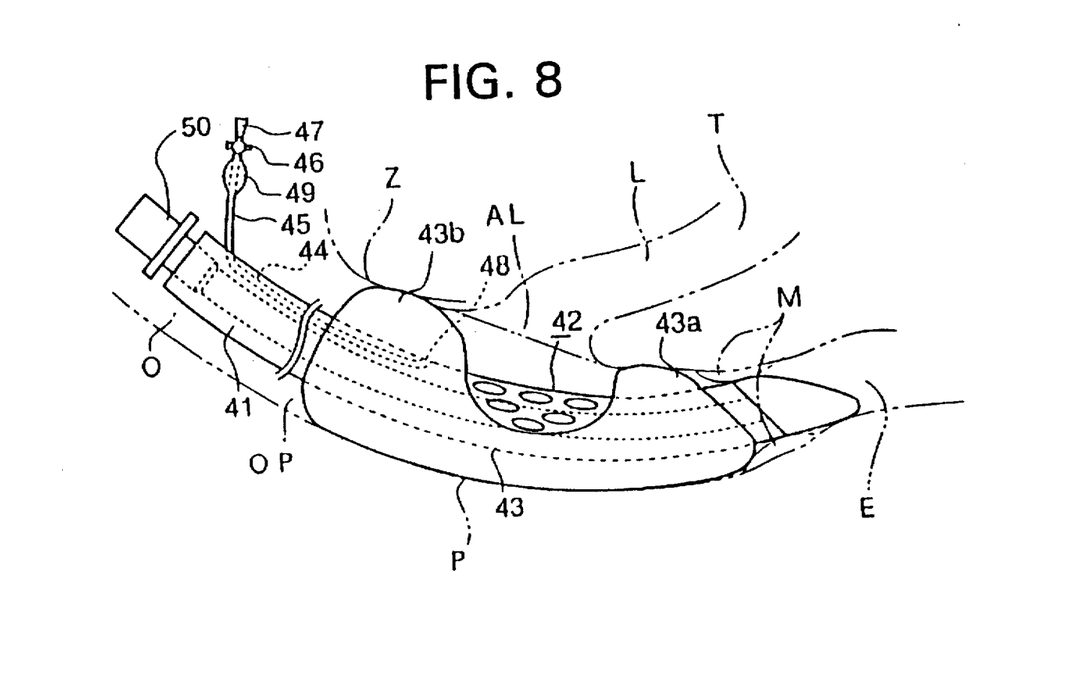
FIG. 8 is a lateral view of the pharyngeal airway of FIG. 6 in a state where the balloon has been fully inflated.

FIG. 6 is a lateral view of a pharyngeal airway in a fourth embodiment according to the present invention, FIG. 7 is a lateral view of the pharyngeal airway of FIG. 6 in a state where the balloon is being slightly inflated, and FIG. 8 is a lateral view of the pharyngeal airway of FIG. 6 in a state where the balloon has been fully inflated.

Referring to FIGS. 6 to 8, a wide bore arched airway tube 41 has a closed, round distal end in a bevelled shape extending toward the proximal end and is provided with a ventilating part 42 near the distal end on the concave or anterior surface thereof. A plurality of longitudinally elongate ventilating pores 42a (for example, nine ventilating pores) are formed in the ventilating part 42 in an even arrangement so as not to reduce the anti-bending strength of the airway tube 41. A balloon 43 is attached to the airway tube 41 at a portion around the ventilating part 42 so as to enclose the distal part of the airway tube 41 and surround the ventilating part 42 when inflated to seal hermetically a transitional part from the lower pharynx to the esophagus, and the laryngeal opening AL.

A small bore gas supply passage 44 is formed longitudinally in the wall of the airway tube 41 so as to open in a pore 48 opening into the interior of the balloon 43. A tube 45 fitted at its proximal end with a cock 46 with a pilot balloon 49 connected to an adaptor 47 is connected to the proximal end of the gas supply passage 44. The adaptor 47 is connected to an implement for supplying a gas into and removing a gas from the balloon 43 to inflate and shrink the balloon 43, such as an injection syringe.

There is no particular restriction on the materials forming the airway tube 41 and the balloon 43 of the pharyngeal airway, and the airway tube 41 and the balloon 43 may be formed of any suitable materials generally used for manufacturing medical implements, provided that those materials are highly safe, soft and flexible; soft vinyl resins and silicone rubbers are suitable materials. The balloon 43 having a part capable of naturally maintaining a bulged shape and the rest part capable of naturally maintaining a shrunk shape can be easily formed by selectively determining the thickness and the hardness of the material forming the balloon 43.

The operation of the pharyngeal airway in the fourth embodiment will be described hereinafter. Referring to FIG. 7, when inserting the airway tube 41 of the pharyngeal airway through the oral cavity 0 in the lower pharynx P, the balloon 43 is evacuated and held in a flat shape with negative pressure as shown in FIG. 6 and is coated with a lubricant, because the oropharyngeal cavity OP is curved and is pressed narrow by the root Z of the tongue when the distal end of the airway tube 41 passes the oropharyngeal cavity OP. After the round distal end of the airway tube 41 along the backside has passed the oropharyngeal cavity OP and has reached the lower pharynx P without catching the laryngeal opening AL, the cock 46 fitted in the proximal end of the tube 45 is opened to apply the atmospheric pressure to the interior of the balloon 43. Then, the distal part 43a of the balloon 43 on the distal side of the ventilating part 42 inflates naturally in a shape as shown in FIG. 7, and the airway tube 41 can be easily advanced as far as the balloon 43 is obstructed by the lower pharynx P behind the laryngeal opening AL and the esophageal sphincter M narrowing the transitional portion to the upper part of the esophagus E.

In this state, where the balloon 43 is obstructed by the esophageal sphincter M, a gas is supplied through the tube 45 and the gas supply passage 44 into the balloon 43. Then, the soft and flexible balloon 43 is inflated in all directions, i.e., longitudinally, transeversely and backwardly the distal part 43a of the balloon 43 comes into light sealing contact with the entire surface of the lower pharynx P, the proximal part 43b of the balloon 43 comes into light sealing contact with the periphery of the laryngeal opening AL and the inner surface of the lower pharynx, and the ventilating part 42 are disposed opposite to the laryngeal opening AL to secure an airway communicating with the larynx L.

When a connector 50 meeting the international standards for positive pressure artificial respiration is connected to a resuscitator, not shown, and a gas, i.e., air or oxygen, is forced intermittently into the airway tube 1, the gas flows through the airway tube 41 and is forced to flow through the ventilating part 42 of the airway tube 41 and the larynx L into the trachea T for inspiration. When the pressure is removed, a gas flows in the reverse direction for expiration.

The balloon 43 is formed of a soft, stretchable thin film so that the balloon 43 conforms closely to the undulated mucosa forming the surface of the lower pharynx for airtight sealing under the atmospheric pressure when the pressure of the gas in the balloon 43 is about 30 cm H₂O or below and is capable of achieving perfect sealing without injuring the mucosa in contact therewith. When conducting intermittent positive pressure artificial ventilation by intermittently applying a gas pressure above that pressure through the airway tube 41, the gas pressure, i.e., a positive pressure in the respiratory tract, acts through the ventilating part 42 disposed opposite to the laryngeal opening AL on the outer surface of the balloon 43 sealing the periphery thereof, so that the flexible balloon 43 is locally deformed and compressed and the internal pressure of the balloon 43 is raised intermittently to a pressure equal to the internal pressure of the airway as shown in FIG. 5, whereby the airtightness can be naturally secured.

Figure 9:
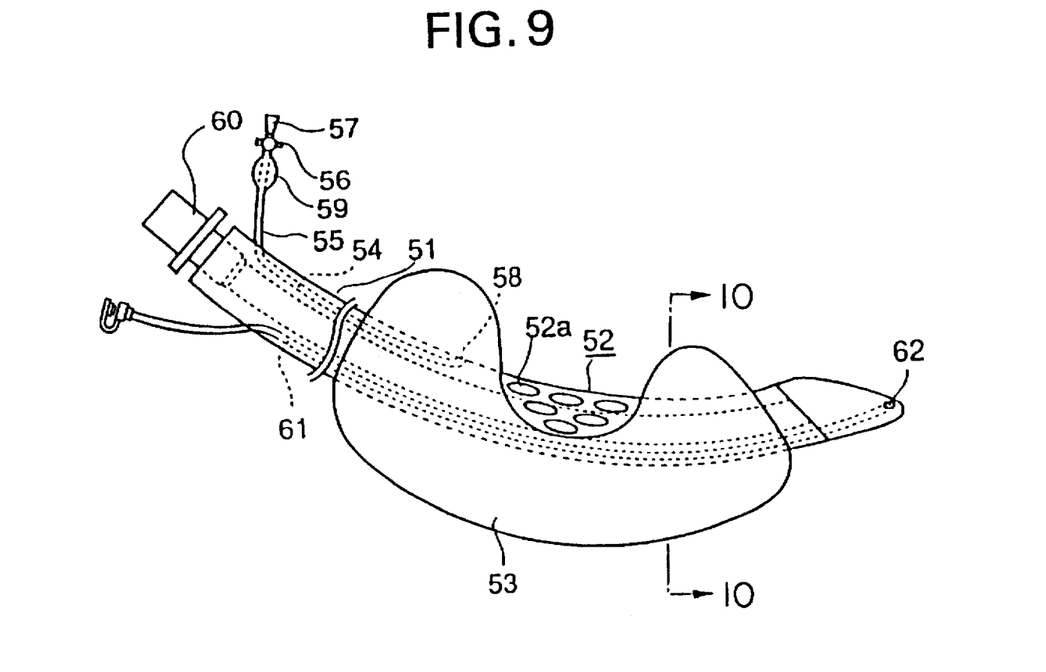
FIG. 9 is a lateral view of a pharyngeal airway when the balloon is inflated in a fifth embodiment according to the present invention.
Figure 10:
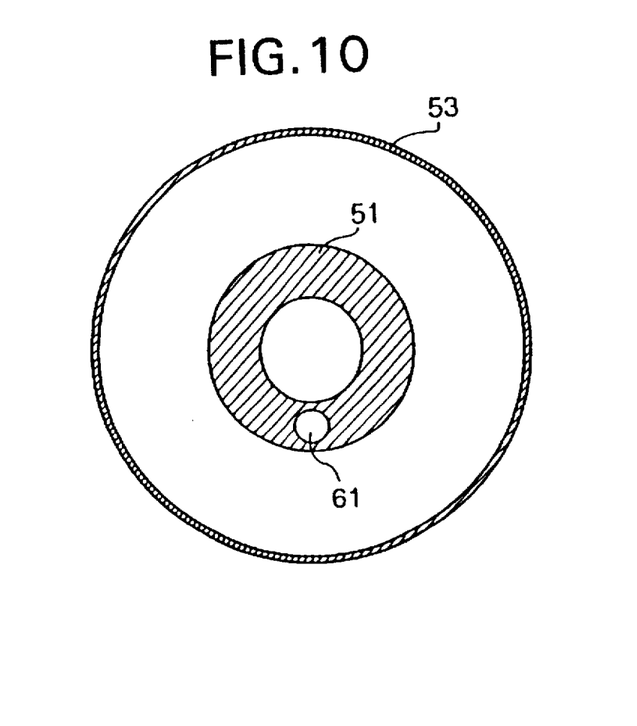
FIG. 10 is an enlarged cross-sectional view taken on the line 10—10 in FIG. 9.

FIG. 9 is a side view of a pharyngeal airway in a fifth embodiment according to the present invention, and FIG. 10 is an enlarged cross-sectional view taken on the line A—A in FIG. 9. An arched airway tube 51 has, similarly to the arched airway tube 41 of the fourth embodiment shown in FIG. 6, a closed, round distal end and a ventilating part 52 in a recessed surface near the distal end. The airway tube 51 is provided with the ventilating part 52 of a plurality of ventilating holes 52a on the recessed surface.

A balloon 53 is attached to the airway tube 51 so as to enclose the distal part of the airway tube 51 and surround the ventilating part 52 when inflated. FIGS. 9 and 10 show such states in which the balloon 23 is inflated.

A small bore gas supply passage 54 is formed longitudinally in the wall of the airway tube 51 so as to open in a pore 58 opening into the interior of the balloon 53. A tube 55 fitted at its proximal end with a cock 56 provided with a pilot balloon 59 connected to an adaptor 57 is connected to the proximal end of the gas supply passage 54. A suction passage 61 for sucking out gastric and esophageal discharges is formed from a position near the proximal end of the airway tube 51 fitted with a connector 60 through the wall of the airway tube 51 so as to open in a suction opening 62 at the distal end of the airway tube 51.

Preferably, the suction passage 31 has a diameter in the range of about 3 to about 5 mm and a circular or an elliptic cross section. When using the pharyngeal airway of FIG. 9, the airway tube 51 is inserted in the pharynx with the balloon 53 evacuated to shrink the balloon 53, the insertion of the airway tube 51 is stopped when the distal end of the airway tube 51 reaches the lower pharynx P and the distal end is obstructed by the esophageal sphincter M in the upper part of the esophagus E. After confirming that air is flowing through the respiratory tract, the balloon 53 is inflated and pressure artificial respiration is started. Then, there is formed a support of the proximal part of the balloon 53 to press the airway opening 52 against the periphery of the laryngeal opening AL to hold the airway tube 51 in place, and the distal part of the balloon 53 is pressed against the lower pharynx P and the inner surface of the esophagus E to enhance the sealing effort between the balloon 53 and the laryngeal opening AL so that the sealing effort of the balloon 53 is able to withstand the maximum inhalation pressure for possitive pressure respiration.

Even if the gas staying in the stomach and the gastric juice regurgitate, the leakage of the gas and the gastric juice into the respiratory tract can be prevented by positively removing the gas and the gastric juice by suction through the suction passage 61.

CAPABILITY OF EXPLOITATION IN INDUSTRY

The pharyngeal airway of the present invention, not to be inserted in the trachea, can be easily inserted through the oral cavity in the lower pharynx, obstructs a transitional region from the lower pharynx to the esophagus, and seals the periphery of the laryngeal opening in an airtight state to secure an airway for positive pressure artificial ventilation. The pharyngeal airway of the present invention is safe, reliable, easy to use and very effective for use as an implement for emergency artificial ventilation.

We claim:

1. A pharyngeal airway selected from the group consisting of:

(A) a pharyngeal airway comprising an arched airway wide bore tube having a bevelled opening formed by diagonally cutting the distal end thereof; and a balloon formed of a soft, flexible thin film, connected to the edge of the bevelled opening and the circumference of a part of the airway tube behind the bevelled opening, and capable of being inflated in a hemispherical shape so as to surround the circumference of a portion of the airway tube behind the distal end of the airway tube; said airway tube being provided with a longitudinal small bore gas passage or tube for passing a gas to inflate or shrink the balloon, longitudinally extending through the wall of the airway tube, having a distal end opening into the balloon and a proximal end having a small bore tube fitted with a connector through which the gas is pumped into and discharged from the balloon;

(B) a pharyngeal airway comprising an arched airway tube having a bevelled opening formed by bevelling the distal end thereof; a first balloon formed of a soft, flexible thin film, connected to the edge of the bevelled opening and the circumference of a part of the airway tube behind the bevelled opening, and capable of being inflated in a ring shape so as to surround the circumference of a portion of the airway tube behind the distal end of the airway tube; and a second balloon formed of a soft, flexible thin film connected to a part of the airway tube near and behind the first balloon and on the side opposite the bevelled opening; said airway tube being provided with two longitudinal small bore gas passages or tubes for supplying a gas to inflate the first and second balloons, longitudinally extending through the wall of the airway tube, having distal ends opening into the first balloon and second balloons, respectively, and proximal ends having small bore tubes fitted with connectors through which the gas is pumped into and discharged from the first and the second balloons, respectively; and (C) a pharyngeal airway comprising an arched airway tube having a closed, round distal end and provided with a plurality of ventilating side holes in a ventilating part of the airway tube near the distal end; and a balloon formed of a soft, flexible thin film, and attached to the airway tube at a part around the ventilating part of the airway tube so as to enclose the distal part of the airway tube and surround the ventilating part of the airway tube when inflated to seal a transitional part from the lower pharynx to the esophagus, and the periphery of laryngeal opening; a small bore gas supply passage being formed longitudinally in the wall of the airway tube so as to open in a pore opening into the interior of the balloon, a tube fitted at its proximal end with a connector for supplying a gas into and discharging the gas from balloon being connected to the proximal end of the gas supply passage.

2. A pharyngeal airway as defined in claim 1 comprising:
an arched airway wide bore tube having a bevelled opening formed by diagonally cutting the distal end thereof; and a balloon formed of a soft, flexible thin film, connected to the edge of the bevelled opening and the circumference of a part of the airway tube behind the bevelled opening, and capable of being inflated in a hemispherical shape so as to surround the circumference of a portion of the airway tube behind the distal end of the airway tube;

said airway tube being provided with a longitudinal small bore gas passage or tube for passing a gas to inflate or shrink the balloon, longitudinally extending through the wall of the airway tube, having a distal end opening into the balloon and a proximal end having a small bore tube fitted with a connector through which the gas is pumped into and discharged from the balloon.

3. A pharyngeal airway according to claim 1, wherein the balloon is capable of shrinking in a flat shape when a negative pressure prevails therein, and has a part on a side opposite the bevelled opening, capable of maintaining a naturally bulged shape and a part on the side of the bevelled opening, capable of maintaining a naturally shrunk shape when the atmospheric pressure prevails in the balloon.

4. A pharyngeal airway according to claim 1, further comprising an inner balloon formed of a stretchable thin film and disposed within said balloon, wherein one or a plurality of side holes are provided in a part of the airway tube surrounded by the inner balloon.

5. A pharyngeal airway as defined in claim 1 comprising:

an arched airway tube having a bevelled opening formed by bevelling the distal end thereof;

a first balloon formed of a soft, flexible thin film, connected to the edge of the bevelled opening and the circumference of a part of the airway tube behind the bevelled opening, and capable of being inflated in a ring shape so as to surround the circumference of a portion of the airway tube behind the distal end of the airway tube; and a second balloon formed of a soft, flexible thin film connected to a part of the airway tube near and behind the first balloon and on the side opposite the bevelled opening;

said airway tube being provided with two longitudinal small bore gas passages or tubes for supplying a gas to inflate the first and second balloons, longitudinally extending through the wall of the airway tube, having distal ends opening into the first balloon and second balloons, respectively, and proximal ends having small bore tubes fitted with connectors through which the gas is pumped into and discharged from the first and the second balloons, respectively.

6. A pharyngeal airway according to claim 5, wherein said airway tube is provided with a gas or liquid passage of a diameter in the range of 3 to 5 mm, having a circular or an elliptic cross section, longitudinally extending through the wall of the airway tube, having a distal end opening in the distal end of the airway tube and a proximal end connected to a suction connector.

7. A pharyngeal airway according to claim 5, wherein the first balloon is capable of shrinking in a flat shape when a negative pressure prevails therein and of maintaining a naturally bulged shape when the atmospheric pressure prevails therein.

8. A pharyngeal airway according to claim 1, wherein the airway tube is formed of a shape memory material soft and flexible at a room temperature, has a cross section having the shape of a rather flat ellipse with its major axis parallel to the transverse direction of the bevelled opening formed by bevelling the distal end of the airway tube or the shape of a rectangle having rounded corners, memorizes an arched shape concave toward the side of the bevelled opening, and arches almost in the memorized arched shape when heated at a temperature around 36° C.

9. A pharyngeal airway according to claim 1, further comprising an inner tube of a moderate diameter extended longitudinally through the airway tube, and having a distal end opening at the distal end of the airway tube and a proximal end connected to a suction connector.

10. A pharyngeal airway as defined in claim 1 comprising:

an arched airway tube having a closed, round distal end and provided with a plurality of ventilating side holes in a ventilating part of the airway tube near the distal end; and a balloon formed of a soft, flexible thin film, and attached to the airway tube at a part around the ventilating part of the airway tube so as to enclose the distal part of the airway tube and surround the ventilating part of the airway tube when inflated to seal a transitional part from the lower pharynx to the esophagus, and the periphery of laryngeal opening;

a small bore gas supply passage being formed longitudinally in the wall of the airway tube so as to open in a pore opening into the interior of the balloon, a tube fitted at its proximal end with a connector for supplying a gas into and discharging the gas from balloon being connected to the proximal end of the gas supply passage.

11. A pharyngeal airway according to claim 10, wherein the balloon is capable of shrinking in a flat shape when a negative pressure prevails therein, and has a distal part on the distal side of the ventilating part, capable of maintaining a naturally bulged shape when the atmospheric pressure prevails therein, and a proximal part on the proximal side of the ventilating part, capable of maintaining a naturally shrunk shape under the atmospheric pressure.

12. A pharyngeal airway according to claim 10, wherein the balloon is formed of a soft, flexible thin film, and is capable of shrinking in a flat shape when a negative pressure prevails therein, of maintaining a naturally bulged shape when the atmospheric pressure prevails therein, and of being inflated by a comparatively low pressure when a possitive pressures prevails therein so as to conform closely to the undulating mucosa forming the surface of the pharynx in an airtight state.

13. A pharyngeal airway according to claim 10, wherein the airway tube is provided in the ventilating part with a plurality of longitudinally elongate ventilating holes formed and in an even array arranged on an airway tube so as not to reduce the anti-bending strength of the airway tube.

14. A pharyngeal airway according to claim 10, further comprising a suction tube extended longitudinally through the airway tube, and having a distal end opening at the distal end of the airway tube and a proximal part connected to a suction connector.

15. A pharyngeal airway according to claim 1, wherein the round distal end of the airway tube is made in a bevelled shape extending toward the dorsal side or along the backside thereof, and the distal part of the airway tube is formed almost straight.

16. A pharyngeal airway according to claim 2, wherein the airway tube is formed of a shape memory material soft and flexible at a room temperature, has a cross section having the shape of a rather flat ellipse with its major axis parallel to the transverse direction of the bevelled opening formed by bevelling the distal end of the airway tube or the shape of a rectangle having rounded corners, memorizes an arched shape concave toward the side of the bevelled opening, and arches almost in the memorized arched shape when heated at a temperature around 36° C.

17. A pharyngeal airway according to claim 5, wherein the airway tube is formed of a shape memory material soft and flexible at a room temperature, has a cross section having the shape of a rather flat ellipse with its major axis parallel to the transverse direction of the bevelled opening formed by bevelling the distal end of the airway tube or the shape of a rectangle having rounded corners, memorizes an arched shape concave toward the side of the bevelled opening, and arches almost in the memorized arched shape when heated at a temperature around 36° C.

18. A pharyngeal airway according to claim 4, further comprising an inner tube of a moderate diameter extended longitudinally through the airway tube, and having a distal end opening at the distal end of the airway tube and a proximal end connected to a suction connector.

* * * * *

UNITED STATES PATENT AND TRADEMARK OFFICE
CERTIFICATE OF CORRECTION

PATENT NO. : 5,743,258
DATED : April 28, 1998
INVENTOR(S) : Toru SATO et al.

It is certified that error appears in the above-indentified patent and that said Letters Patent is hereby corrected as shown below:

On the title page:

Item [73] should read
--Assignee: Toru SATO, Yonago-shi, Tottori, Japan; and Mallinckrodt Medical, Inc., St. Louis, MO--.

Signed and Sealed this

Tenth Day of November 1998

Attest:

BRUCE LEHMAN

*Attesting Officer*  *Commissioner of Patents and Trademarks*